(12) United States Patent  
Minkoff et al.

(10) Patent No.: US 6,915,153 B2  
(45) Date of Patent: Jul. 5, 2005

(54) CATHETER ANTENNA FOR MAGNETIC RESONANCE IMAGING

(75) Inventors: Lawrence A. Minkoff, Lattingtown, NY (US); Valentin Fuster, New York, NY (US); Meir Shinnar, Teaneck, NJ (US); Zahi A. Fayad, New York, NY (US); Juan J. Badimon, Larchmont, NY (US)

(73) Assignees: Magna-Lab Inc., Syosset, NY (US); Mount Sinai School of Medicine of the City University of New York, New York, NY (US)

( * ) Notice: Subject to any disclaimer, the term of this patent is extended or adjusted under 35 U.S.C. 154(b) by 135 days.

(21) Appl. No.: 10/101,521

(22) Filed: Mar. 18, 2002

(65) Prior Publication Data

US 2003/0023160 A1 Jan. 30, 2003

Related U.S. Application Data

(63) Continuation of application No. 09/517,894, filed on Mar. 3, 2000, now abandoned.

(51) Int. Cl.$^7$ .............................................. A61B 5/055
(52) U.S. Cl. ........................ 600/423; 324/318; 324/322
(58) Field of Search ................................ 600/410, 411, 600/421, 422, 423; 324/307, 309, 318, 322

(56) References Cited

U.S. PATENT DOCUMENTS 5,699,801 A * 12/1997 Atalar et al. ................. 600/410  
6,060,882 A * 5/2000 Doty ........................... 324/318

* cited by examiner

*Primary Examiner*—Eleni Mantis Mercader  
(74) *Attorney, Agent, or Firm*—Darby & Darby

(57) ABSTRACT

The magnetic resonance catheter antenna includes a first tube having a proximal end and a distal end. A litz wire has a first end and a second end and is looped within the first tube such that the first end and the second end are disposed at the proximal end. A guide wire is disposed within the first tube. A multifilament or solid wire may be used instead of a litz wire. At least the looped portion of the wire is insulated.

19 Claims, 1 Drawing Sheet

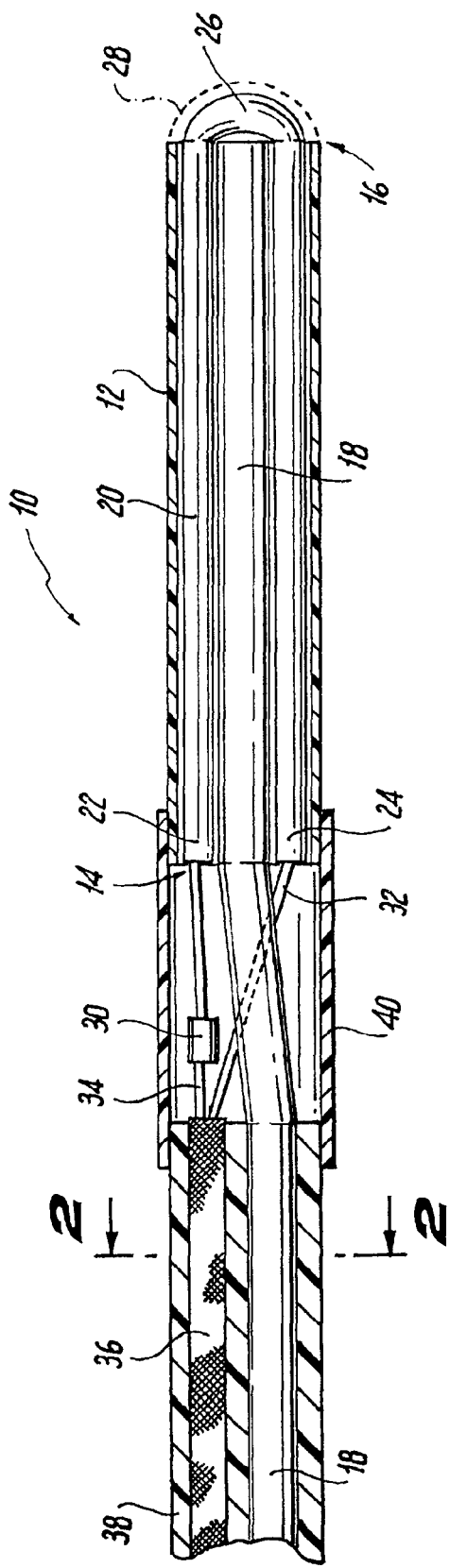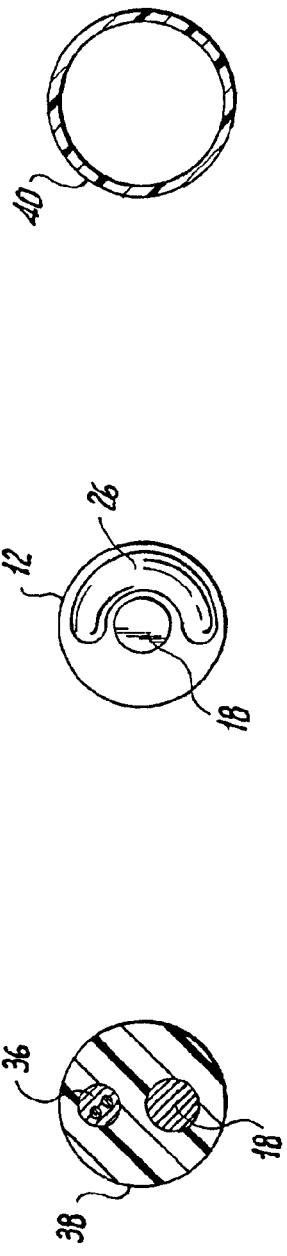

US 6,915,153 B2

CATHETER ANTENNA FOR MAGNETIC RESONANCE IMAGING

CROSS REFERENCE TO RELATED APPLICATIONS

This is a continuation of U.S. Ser. No. 09/517,894, filed on Mar. 3, 2000, now abandoned. This prior application is hereby incorporated herein by reference, in its entirety.

BACKGROUND OF THE INVENTION

1. Field of the Invention

The present invention relates to a magnetic resonance ("MR") catheter antenna and method of using the same.

2. Discussion of the Related Art

The advantageous use of magnetic resonance technology in provided safe, rapid images of an internal portion of a patient has long been known. But to obtain an image of a vessel within the body, it is necessary to introduce an invasive probe within that vessel. To provide an MR image, the probe has a receiving coil therein. RF pulses are provided to the region of interest to excite magnetic resonance signals. Gradient magnetic pulses are applied to the region of interest with the receiver coil receiving magnetic resonance signals and emitting responsive output signals, which may be processed by a computer to provide image information for display in a desired manner.

To image even the smallest internal passageways, such as, for example, arteries emanating from the heart, it is necessary to employ a flexible receiver coil. In addition, the probe should have a very small outer diameter so that it may be inserted inside the artery so that a magnetic resonance image thereof can be obtained.

U.S. Pat. No. 5,699,801 to Atalar et al. discloses a receiver 8 that it is in the form of coil 22. Coil 22 has a pair of electrodes 24, 26 that are generally parallel and are spaced apart from each other. The electrodes 24, 26 are embedded in a dielectric material 30, and the ends of the conductors 24, 26 are electrically connected by wire 32. Coil 22 is disclosed as a having a width D of about 0.5 to 2.0 cm. The conductors 24, 26 have an individual diameter of about 0.1 mm to 3 mm. Thus, coil 22 is embedded in a dielectric material 30 (i.e., TEFLON®), which requires that the practical diameter of any coil built in accordance with the teachings of the '801 patent will have a diameter that is too large to be placed in relatively small arteries adjacent to the heart. In accordance with the teachings of the '801 patent, the dielectric material 30 should be resilient to permit flexing of the coil so that it will return to its original position. Thus, the probe will place stress and may perforate through an artery wall as it returns to its original position. The dielectric material 30 must be sufficiently rigid to resist undesired deformation of the spacing D between the conductors 24, 26. Thus, the coil will not be flexible enough to be guided through these arteries.

There still exists a need in the art to provide a probe that can be sized to fit within relatively small arteries so that an MR image of these vessels can be obtained. There still further exists a need for a probe that can be guided with a guide wire while being insertable into these arteries to facilitate the insertion of the probe into these arteries.

SUMMARY OF THE INVENTION

It is an object of the present invention to provide an intra-vascular catheter that includes an MR probe so that an MR image can be obtained. It is a further object of the present invention to provide the probe with a guide wire so that it can be directed through relatively small vessels, such as, for example, arteries.

These and other objects are achieved, in accordance with an exemplary embodiment of the present invention, which includes, a first tube having a proximal end and a distal end. A litz wire has a first end and a second end looped within the first tube such that the first end and the second end are disposed at the proximal end.

In accordance with another embodiment of the present invention, a guide wire is disposed within the first tube.

In accordance with yet another embodiment of the present invention, a multifilament or solid wire is used instead of a litz wire. At least the looped portion of the wire is insulated.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a cross-sectional view of the magnetic resonance catheter antenna according to the present invention;

FIG. 2 is a cross-sectional view taken along lines 2—2 of FIG. 1 and looking in the direction of the arrows;

FIG. 3 is a right end view of the apparatus of FIG. 1; and

FIG. 4 is a cross-sectional view of the third tube connecting the first tube to the second tube.

DETAILED DESCRIPTION OF THE PREFERRED EMBODIMENT

Referring now to FIGS. 1–4, a magnetic resonance catheter antenna 10 in accordance with the present invention is illustrated. The apparatus includes a first tube 12 having a proximal end 14 and a distal end 16. First tube 12 has a maximum outer diameter of 1.5 mm, and is preferably about 1.4 mm in diameter. A guide wire 18 is disposed within first tube 12. A first wire 20 has a first end 22 and a second end 24. Wire 20 is looped within first tube 12 about guide wire 18 such that first end 22 and second end 24 are disposed at the proximal end 14 of first tube 12. First wire 20 has a U-shaped looped portion 26 disposed at distal end 16 of first tube 12. In use, within the body, looped portion 26 must be insulated to prevent the conducting portion of wire 20 from contacting the body. In addition or alternative to insulating looped portion 26, first tube 12 may include a semi-hemispherical shaped cap 28, as illustrated by dashed lines in FIG. 1, to insulate looped portion 26 of first wire 20 from the ambient atmosphere.

First end 22 of first wire 20 is electrically connected to a capacitor 30. A third wire 32 is electrically connected to first wire 20 at second end 24 thereof. A fourth wire 34 is electrically connected to capacitor 30. Wires 32 and 34 are joined to form coaxial cable 36. Coaxial cable 36 and guide wire 18 are disposed within a second tube 38. Second tube 38 is provided with two lumens, one to receive guide wire 18 and the other lumen to received coaxial cable 36.

A third tube 40 is used to connect the first tube 12 to second tube 38. Third tube 40 encloses capacitor 30. Third tube 40 is preferably made from a sufficiently flexible silicon tubing that has a durometer of about 50. However, the durometer of the silicon tubing 40 can be as soft as 35.

Wire 20 can be formed from litz wire, multi-stranded wire or solid copper wire. Currently, litz wire is preferred because each strand is individually insulated. In a currently preferred embodiment, the litz wire has a size that is approximately equivalent to 30 AWG solid wire. In a currently preferred embodiment, approximately 10 strands of 40 gage wire having an equivalent of 34 AWG solid copper wire has been used. If solid wire is used, 30 AWG wire is preferred.

Having described the presently preferred exemplary embodiment of magnetic resonance catheter antenna in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

What is claimed is:

1. A magnetic resonance catheter antenna apparatus comprising:
   a first tube having a proximal end and a distal end;
   a second tube;
   a third tube connecting said first tube to said second tube having a durometer of about 50; and
   a litz wire having a first end and a second end looped within said first tube such that said first end and said second end are disposed at said proximal end wherein said litz wire is at least one of a size that is approximately equivalent to 30 AWG solid wire and is comprised of about ten strands, each strand having a size equivalent to about 40 AWG;
   wherein said magnetic resonance catheter antenna is adapted to be placed within small vessels such as the coronary arteries and veins.

2. The magnetic resonance catheter antenna according to claim 1, wherein one of said ends of said litz wire is electrically connected to a capacitor.

3. The magnetic resonance catheter antenna according to claim 2, wherein said second tube having at least one lumen for receiving a second wire that is electrically connected to said capacitor, and a third wire that is electrically connected to the other end of said litz wire.

4. The magnetic resonance catheter antenna according to claim 3, wherein said third tube encloses said capacitor.

5. The magnetic resonance catheter antenna according to claim 1, wherein said litz wire has a looped portion disposed at said distal end.

6. The magnetic resonance catheter antenna according to claim 1, wherein said first tube has a lumen therein for receiving a guide wire.

7. The magnetic resonance catheter antenna according to claim 6, wherein said lumen is in the center of said first tube.

8. A magnetic resonance catheter antenna comprising:
   a first tube having a proximal end and a distal end;
   a second tube;
   a third tube connecting said first tube to said second tube having a durometer of about 50;
   a guide wire disposed within said first tube; and
   a first wire being one of litz wire and multi-stranded wire having a first end and a second end looped within said first tube about said guide wire such that said first end and said second end are disposed at said proximal end wherein said first wire is at least one of: a size that is approximately equivalent to 30 AWG solid wire, and comprised of about ten strands, each strand having a size equivalent to about 40 AWG;
   wherein said magnetic resonance catheter antenna is adapted to be placed within small vessels such as the coronary arteries and veins.

9. The magnetic resonance catheter antenna according to claim 8, wherein one of said ends of said wire is electrically connected to a capacitor.

10. The magnetic resonance catheter antenna according to claim 9, wherein said second tube having at least two lumens, one of said lumens for receiving a second wire that electrically connects to said capacitor and a third wire that electrically connects to the other end of said first wire and a second one of said lumens for receiving said guide wire.

11. The magnetic resonance catheter antenna according to claim 10, wherein said third tube encloses said capacitor.

12. The magnetic resonance catheter antenna according to claim 10, wherein said third tube encloses said capacitor.

13. The magnetic resonance catheter antenna according to claim 8, wherein said guide wire has a diameter of approximately less than or equal to 0.014 inch.

14. The magnetic resonance catheter antenna according to claim 8, wherein said first wire has a looped portion disposed at said distal end.

15. A magnetic resonance catheter antenna comprising:
   a first tube having a proximal end and a distal end;
   a second tube:
   a third tube connecting said first tube to said second tube having a durometer of about 50;
   a multifilament wire having a first end, a second end and a looped portion looped within said first tube such that said first end and said second end are disposed at said proximal end, and said looped portion is disposed at said distal end, at least said looped portion of said wire being insulated wherein said multifilament wire is at least one of: a size that is approximately equivalent to 30 AWG solid wire, and comprised of about ten strands, each strand having a size equivalent to about 40 AWG;
   wherein said magnetic resonance catheter antenna is adapted to be placed within small vessels such as the coronary arteries and veins.

16. The magnetic resonance catheter antenna according to claim 15, wherein one of said ends of said wire is electrically connected to a capacitor.

17. The magnetic resonance catheter antenna according to claim 16, wherein said second tube having at least one lumen for receiving a second wire that is electrically connected to said capacitor, and a third wire that is electrically connected to the other end of said wire.

18. The magnetic resonance catheter antenna according to claim 15, wherein said first tube has a lumen therein for receiving a guide wire.

19. The magnetic resonance catheter antenna according to claim 18, wherein said lumen is in the center of said first tube.

* * * * *